US00PP09678P

United States Patent [19]

Hill, Jr.

[11] Patent Number: Plant 9,678

[45] Date of Patent: Oct. 29, 1996

[54] VRIESEA PLANT NAMED WERNER RAUH

[75] Inventor: Herbert H. Hill, Jr., Lithia, Fla.

[73] Assignee: Twyford International, Inc., Santa Paula, Calif.

[21] Appl. No.: 490,812

[22] Filed: Jun. 15, 1995

[51] Int. Cl.[6] ..... A01H 5/00

[52] U.S. Cl. ..... Plt./88.8

[58] Field of Search ..... Plt./88.8

*Primary Examiner*—James R. Feyrer

*Attorney, Agent, or Firm*—Foley & Lardner

[57] ABSTRACT

A new cultivar of Vriesea named 'Werner Rauh' characterized by its large branched red inflorescence, and dark green glossy foliage. Plants of 'Werner Rauh' grow easily, and resist leaf tip browning and leaf spot problems to which V. poelmanii is prone. The plant tolerates temperature fluctuations from 38°–94° F. without notable damage.

1 Drawing Sheet

The present invention relates to a new and distinct cultivar of Vriesea, a genus within the family bromeliaceae, hereinafter referred to by the cultivar name 'Werner Rauh'. The new cultivar is a hybrid resulting from a cross of parent plants identified below.

Vriesea comprise a genus of more than 200 species of herbaceous evergreen perennials suitable for cultivation in the home or under glass. Vriesea are predominantly epiphytic and are native to the tropics. For the most part the species vary in diameter from 7 or 8 inches to 3 or 4 feet and have rosettes of glossy, smooth edged leaves which may be entirely green or variously marked with bands or variegation.

Floral bracts of Vriesea frequently have brilliant colors and may last for many months. The range of bract colors for Vriesea is generally yellow, orange, red and red-purple. Tubular, three petalled flowers may also appear on the scape from under the colorful bracts, but are usually short lived.

Vriesea may be advantageously grown as pot plants for greenhouse or home use. Desirably the plants are shaded from direct sunlight and the central vase-like part of the leaf rosette is normally filled with water.

Vriesea is native to tropical America. Leaves of the Vriesea are usually arranged in basal rosettes which are stiff and entire and in several vertical ranks. Vriesea have terminal spikes which are bracted. Asexual propagation of Vriesea is frequently done through the use of tissue culture practices. Propagation can also be from off-shoots produced by the plant which may then be rooted. The resulting plantlets are detached from the mother plant and may be potted up in a suitable growing mixture.

The new cultivar 'Werner Rauh' is a product of a planned breeding program and was originated by the inventor Herbert H. Hill Jr., from a cross made during such program in Lithia, Fla. in 1983. The male, or pollen parent, was a selection from *Vriesea* 'Queen'. The female, or seed parent, was a selection from *Vriesea poelmanii* cv. 'Georgia'. The selection comprising the new variety was chosen after commencement of flowering of the progeny in 1987. Subsequent asexual propagation by the iventor in Lithia, Fl by offshoots has demonstrated that the combination of characteristics as herein disclosed for the new cultivar 'Werner Rauh' are firmly fixed and are retained through successive generations of asexual reproduction.

The following combined characteristics distinguish Vriesea 'Werner Rauh' from other cultivars of *V. poelmanii*, including 'Barbara', a leading commerical cultivar characterized by its bright red, long lasting blooms and its medium green glossy foliage.

1. 'Werner Rauh' produces a branched spike with dark red bracts. The foliage is dark green and very shiny.

2. Plants of 'Werner Rauh' resist leaf tip browning and leaf spotting to which *V. poelmanii* are prone.

3. Plants of 'Werner Rauh' tolerate temperature fluctuations from 38°–94° F. without notable damage.

4. Plants of 'Werner Rauh' grow quickly to marketable size, often finishing 3–6 months sooner than plants of *V. poelmanii.*

5. Because of the above-listed characteristics, 'Werner Rauh' is a much easier cultivar to produce.

'Werner Rauh' has not been tested under all available environmental conditions and the phenotype may vary with variations in environmental conditions such as temperature, light intensity, daylength and humidity, without, however any variation in genotype.

The accompanying color photographic drawing shows typical characteristics of 'Werner Rauh', with colors being as nearly true as possible with illustrations of this type. The plant illustrated is a 14–16 month-old plant of 'Werner Rauh' grown from an offshoot and finished in a 15.5 cm pot.

The following description is taken from the plant illustrated on sheet 1.

The plant was grown in Lithia, Fla. by the inventor under greenhouse conditions which are typical of the industry. Color reference are made to The Royal Horticultural Society Colour Chart.

I. Plant:

*Form.*—Basal rosette of strap-like leaves arranged around a central axis.

*Height.*—Approximately 55 cm including inflorescence.

*Diameter.*—Approximately 50 cm.

II. Foliage:

*Size of leaf.*—The basal leaves are approximately 28–33 cm long, and 4.0 – 4.8 cm wide (flattened). At their widest point, near the base, the leaves are approximately 6.5–7.2 cm wide.

*Shape of leaf.*—The leaf blade is ligulate with a cuspidate tip. The margins are entire. The leaves are curved over their length. The leaf is channeled, the tip is somewhat twisted, wavy and curved downward.

*Surface texture.*—The leaf blade is relatively thin, smooth and shiny.

*Color.*—The leaves are dark green throughout. The upper surface is considerably darker and greener than, but closest to, 137 A. The lower surface is darker and greener than, but closest to 147B.

*Average number of leaves.*—The plant produces approximately 30 leaves before producing an inflorescence.

III. Bracts:

*Size and color.*—The floral bracts (with underlying sessile flowers or lateral branch spikes) are approximately 3.5–5.9 cm long, 2.7–3.8 cm wide (flattened), and darker than but closest to 45A in color.

*General shape.*—Individual bracts are triangular, folded in the center, with the base encircling the scape. The bracts are arranged imbricate, and alternate along the scape giving the inflorescence a flattened appearance. The bracts tend to separate from the scape as the flowers emerge.

*Branch spikes.*—The inflorescence has approximately 8 branches. The branches are approximately 10.5–16.0 cm long, 3.0 –4.8 cm wide, and contain approximately 9 –14 flowers.

The scape bracts are approximately 10.5–24.5 cm long, and approximately 4.0–4.7 cm wide and resemble short leaves. The upper surface is greener than but closest to 137A. The lower surface is 147B.

*Number.*—Floral bracts, approximately 98. Scape bracts, approximately 7.

*Texture.*—Smooth and glossy.

*Margin.*—Entire.

*Scape.*—The scape is approximately 49 cm tall, 10 mm in diameter, and 145C with areas greener than but closest to 142A in color.

IV. Flowers:

*Borne.*—Lateral, alternate from under floral bracts along the scape.

*Shape of inflorescence.*—The inflorescence is a tall branched spike with alternate, imbricate bracts, and approximately 8 branch spike.

*Individual flowers.—Length:* The length o the flower is about 6.0 cm, and the length of the sepals is about 3.1 cm. The sepals are greener than but closest to 11B suffused in the middle with 42A. Three sepals are present. *Quantity:* Approximately 94 flowers/buds present depending on the size of plant and inflorescence. Branch spikes are present, each containing approximately 9–14 flowers. *Corolla:* Ligulate, approximately 4.7 cm in length. The petals are 11B with green 151B tips. Three petals are present.

*Time of blooming.*—In mature plants, flowering begins approximately 10–14 weeks after induction, at any time of the year.

*Duration of blooms.*—The inflorescence will hold its color approximately 5–8 months. Individual flowers last 1 day, and the total duration of flowering is about 7–11 weeks.

V. Reproductive organs:

*Ovary.*—Superior, three locules, 5 mm in length.

*Pistil.*—5.2 cm long, 150A in color.

*Stamens.*—Six present, filament 4.1 cm, anthers 8 mm long, yellow 12B in color.

VI. Seed characteristics: Not observed.

I claim:

1. A plant of a new and distinct cultivar of Vriesea plant named 'Werner Rauh' as illustrated and described.

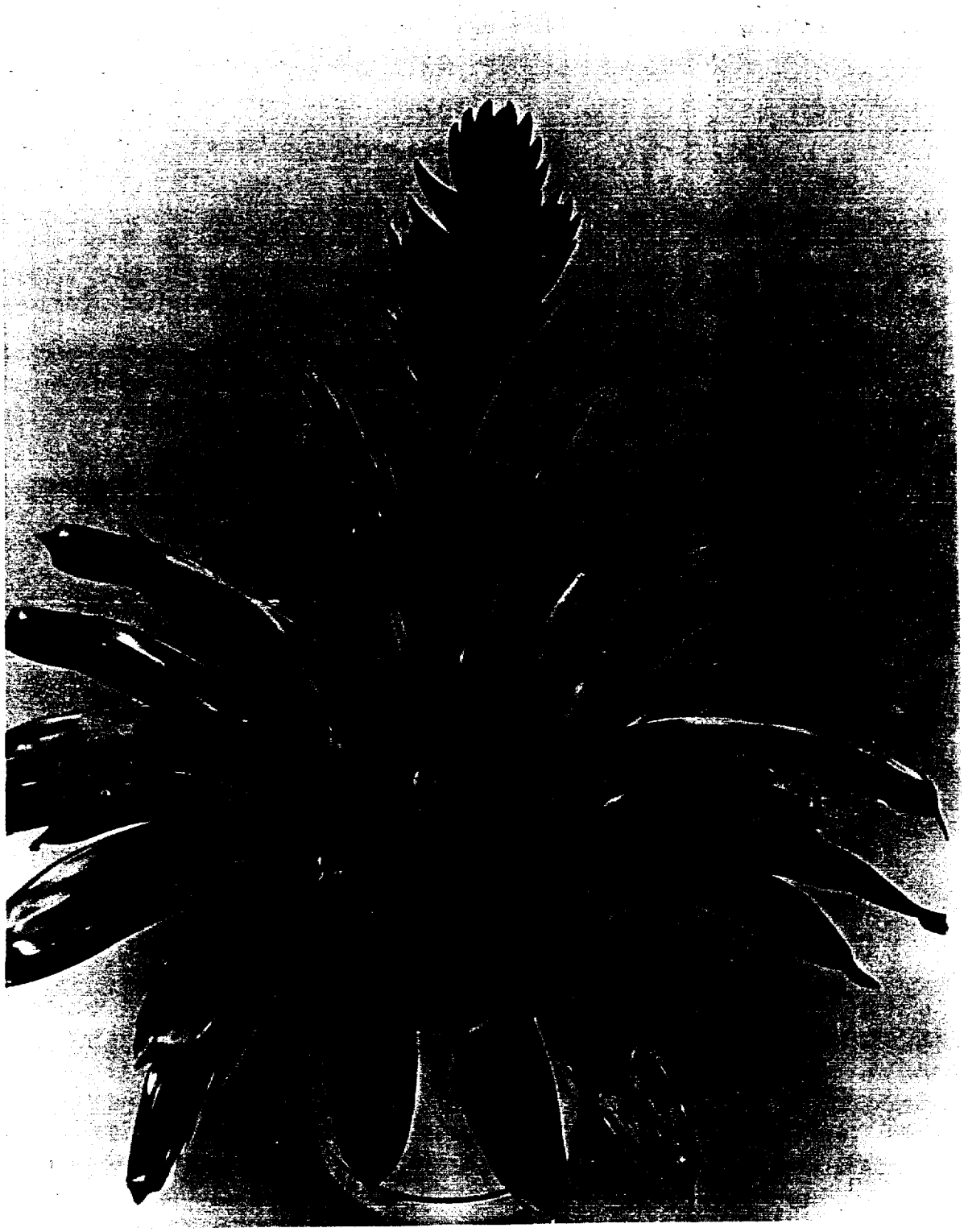

* * * * *